United States Patent
Pardonge

(10) Patent No.: US 9,186,471 B2
(45) Date of Patent: Nov. 17, 2015

(54) FLUID MATERIAL-DISPENSING DEVICE

(75) Inventor: Jean-Marc Pardonge, Les Authieus sur Port St Ouen (FR)

(73) Assignee: APTAR FRANCE SAS, Le Neubourg (FR)

( * ) Notice: Subject to any disclaimer, the term of this patent is extended or adjusted under 35 U.S.C. 154(b) by 632 days.

(21) Appl. No.: 13/505,688

(22) PCT Filed: Nov. 2, 2010

(86) PCT No.: PCT/FR2010/052342
§ 371 (c)(1),
(2), (4) Date: May 2, 2012

(87) PCT Pub. No.: WO2011/055068
PCT Pub. Date: May 12, 2011

(65) Prior Publication Data
US 2012/0222673 A1 Sep. 6, 2012

(30) Foreign Application Priority Data
Nov. 3, 2009 (FR) .................................. 09 57774

(51) Int. Cl.
*A61M 11/00* (2006.01)
*A61M 15/08* (2006.01)
(Continued)

(52) U.S. Cl.
CPC ........... *A61M 15/08* (2013.01); *A61M 15/0065* (2013.01); *A61M 15/0071* (2014.02); *B05B 11/3052* (2013.01); *B65D 83/20* (2013.01); *B65D 83/753* (2013.01)

(58) Field of Classification Search
CPC ............ A61M 15/0065; A61M 15/08; A61M 15/0071; A61M 15/009; A61M 15/0091; A61M 15/0093; B65D 83/20; B65D 83/753; B65D 83/54; G01F 11/02; G01F 11/04
USPC ............. 128/200.14–200.23, 202.22, 202.27, 128/203.22; 604/94.01, 275; 222/36–38, 222/41, 47, 49, 50
See application file for complete search history.

(56) References Cited

U.S. PATENT DOCUMENTS 5,724,957 A * 3/1998 Rubsamen et al. ...... 128/200.14
6,045,003 A * 4/2000 Seidler ........................... 222/48
(Continued)

FOREIGN PATENT DOCUMENTS

| EP | 1 369 139 A1 | 12/2003 |
| WO | 00/51672 A1 | 9/2000 |
| WO | 2008/077623 A1 | 7/2008 |

OTHER PUBLICATIONS

International Search Report for PCT/FR2010/052342 dated Feb. 23, 2011.
(Continued)

*Primary Examiner* — Lynne Anderson
*Assistant Examiner* — Mark K Han
(74) *Attorney, Agent, or Firm* — Sughrue Mion, PLLC

(57) ABSTRACT

A fluid dispenser device having a dispenser member, such as a pump or a valve, that is mounted on a fluid reservoir and that is actuated by a dispenser head that includes a spray orifice. The device further having a visual indicator that is movable between an indicating position and a non-indicating position, the visual indicator being moved into their non-indicating position at the start of each actuation of the dispenser member, and being moved from the non-indicating position towards the indicating position by the fluid, while it is being dispensed.

11 Claims, 2 Drawing Sheets

(51) Int. Cl.
*A61M 15/00* (2006.01)
*B05B 11/00* (2006.01)
*B65D 83/20* (2006.01)
*B65D 83/14* (2006.01)

(56) References Cited

U.S. PATENT DOCUMENTS

| | | | | |
|---|---|---|---|---|
| 6,138,669 | A * | 10/2000 | Rocci et al. | 128/200.23 |
| 7,387,121 | B2 * | 6/2008 | Harvey | 128/203.15 |
| 7,464,708 | B2 * | 12/2008 | Marx | 128/205.23 |
| 8,327,844 | B2 * | 12/2012 | Djupesland | 128/203.22 |
| 8,377,009 | B2 * | 2/2013 | Sullivan et al. | 604/200 |
| 8,567,394 | B2 * | 10/2013 | Herder et al. | 128/203.19 |
| 8,590,742 | B2 * | 11/2013 | Devos et al. | 222/41 |
| 8,869,791 | B2 * | 10/2014 | Sauzade et al. | 128/200.14 |
| 2003/0106550 | A1 * | 6/2003 | Harvey | 128/200.23 |

OTHER PUBLICATIONS

International Preliminary Report on Patentability for PCT/FR2010/052342.

* cited by examiner

FLUID MATERIAL-DISPENSING DEVICE

CROSS REFERENCE TO RELATED APPLICATIONS

This application is a National Stage of International Application No. PCT/FR2010/052342, filed on Nov. 2, 2010, which claims priority from French Patent Application No. 0957774, filed on Nov. 3, 2009, the contents of all of which are incorporated herein by reference in their entirety.

The present invention relates to a fluid dispenser device, and more particularly to a device provided with a visual dose-taking indicator.

BACKGROUND

In fluid dispenser devices that use dispenser members such as pumps or valves for performing the dispensing, the fluid dispensed is generally finely sprayed in the form of a spray. For medical devices of the type for dispensing medication nasally, the dose of fluid dispensed may be small, and the fluid may be dispensed in the form of a spray that is particularly fine. The user then cannot always tell whether the fluid has been effectively dispensed. Various dose-counting systems exist for informing the user about the number of doses that have been dispensed or that remain to be dispensed from the dispenser device. However, such counters or indicators are generally actuated in mechanical manner while the device is being actuated, and they thus represent device actuations, rather than the effective dispensing of fluid through the dispenser orifice. In the event of a malfunction, a dose may be counted without being effectively dispensed to the user. Documents WO 2008/077623 and WO 00/51672 describe prior-art devices.

BRIEF SUMMARY

An object of the present invention is to provide a fluid dispenser device that does not have the above-mentioned drawbacks.

More particularly, an object of the present invention is to provide a fluid dispenser device that indicates to the user that a dose has been effectively taken, i.e. the fluid has been effectively dispensed through the spray orifice.

Another object of the present invention is to provide a fluid dispenser device that provides reliable information to the user with regard to effective dispensing of the dose.

Another object of the present invention is to provide a fluid dispenser device that is simple and inexpensive to manufacture and to assemble.

The present invention thus provides a fluid dispenser device comprising a dispenser member, such as a pump or a valve, that is mounted on a fluid reservoir and that is actuated by a dispenser head that includes a spray orifice, said device further comprising visual indicator means that are movable between an indicating position and a non-indicating position, said visual indicator means being moved into their non-indicating position at the start of each actuation of said dispenser member, and being moved from said non-indicating position towards said indicating position by said fluid, while it is being dispensed.

Advantageously, said visual indicator means are arranged inside said dispenser head, and can be seen, at least in part, from the outside, in their indicating position.

Advantageously, said visual indicator means include a movable member that is urged by a spring towards its non-indicating position, and that is urged by the pressure of the fluid during dispensing towards its indicating position.

Advantageously, said movable member is blocked in the indicating position by a blocking element that is urged resiliently towards its blocking position.

Advantageously, said blocking element is released from its blocking position at the start of actuation of the dispenser member, thereby enabling the movable member to return to its non-indicating position, under the effect of said spring.

Advantageously, said blocking element includes at least one flexible tab that is provided with an inner profile that co-operates with a radial projection of said movable member so as to hold said movable member in its indicating position.

Advantageously, said at least one flexible tab includes an end projection that, at the start of actuation of the dispenser member, co-operates with a cam that is adapted to deform said at least one flexible tab radially outwards, eliminating said co-operation between the inner profile of the flexible tab and the radial projection of the movable member.

Advantageously, said end projection includes a sloping bottom end surface that co-operates with the cam at the start of actuation so as to deform each flexible tab radially outwards, and a sloping top surface that co-operates with the cam after actuation so as to deform each flexible tab radially inwards while the dispenser head is returning to its rest position.

Advantageously, said cam is formed by a rounded projection that is secured to the reservoir, in particular that is secured to the fastener ring that fastens the dispenser member on said reservoir.

Advantageously, said movable member is hollow and defines said spray orifice of the device.

Advantageously, said movable member projects axially out from said dispenser head in the indicating position, said portion projecting out from the head forming a visual indicator that can be seen from the outside.

Advantageously, said movable member contains an insert that cannot move relative to said movable member.

Advantageously, said dispenser head is a nasal head including an axial extension for penetrating into a user's nostril.

BRIEF DESCRIPTION OF THE DRAWINGS

These and other characteristics and advantages of the present invention appear more clearly from the following detailed description of a particular embodiment thereof, given by way of non-limiting example, and with reference to the accompanying drawing, in which.

DETAILED DESCRIPTION

The present invention relates to a mechanical dose-expulsion indicator. The present invention applies more particularly to fluid dispensers in the field of pharmacy, and in particular to nasal-type dispensers, but naturally the present invention could also apply to other fields of application.

The principle of the invention consists in providing a movable mechanical element that is moved from a non-indicating position to an indicating position by the pressure of the fluid while it is being dispensed. The term "indicating position" means a position that indicates that a dose of fluid has been dispensed effectively through the spray orifice during the previous actuation of the device. The term "non-indicating position" means a position that, on the contrary, indicates that a dose of fluid has not been dispensed effectively. Thus, after using the device, the user sees the indicator in its indicating position, thereby guaranteeing that the dose has been dispensed. The indicator then remains in its indicating position until the next actuation of the device, and it is blocked in this position by a blocking element. At the moment of the next actuation, when the user takes hold of the device, the user sees the indicator in its indicating position. At the very start of the actuation stroke of the device, the indicator is returned to its non-indicating position. It should be observed that for a nasal-type dispenser device in which the user inserts a nasal extension of the dispenser head of said device into a nostril, the user thus cannot see the indicator returning to its non-indicating position at the very start of the actuation stroke. Then, when the fluid is effectively dispensed, generally towards the end of the actuation stroke of the device, the pressure of the fluid being dispensed automatically returns said indicator into its indicating position. The passage via the non-indicating position at the very start of actuation guarantees to the user that the indicating position means that the dose of fluid has indeed been dispensed effectively. If the dose is not emitted, the indicator remains in its non-indicating position, since it is not returned to its indicating position by the pressure of the fluid being dispensed.

The figures show a particular embodiment of the present invention. It should be observed that this embodiment is only one example, and that the invention is not limited to this embodiment. In particular, The visual indicator means 50 could be made in some other way.

Figure 1:
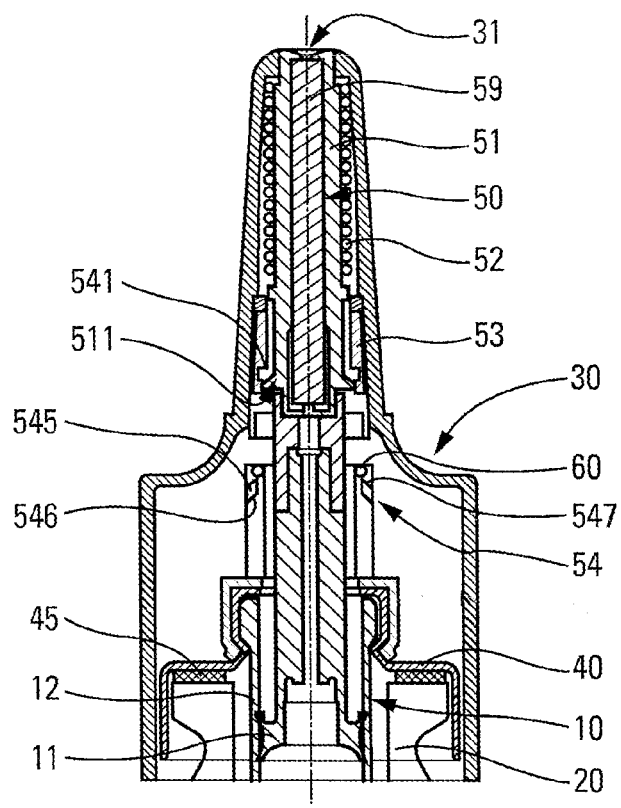
FIG. 1 is a diagrammatic section view of a fluid dispenser device in an advantageous embodiment of the present invention, shown in its non-indicating position.

In the device shown in FIG. 1, a dispenser member 10, specifically a pump, is mounted on a reservoir 20 (of which only the neck is shown) by means of a fastener ring 40, with a neck gasket 45 being interposed therebetween. In conventional manner, a piston 11 slides in leaktight manner in a pump body 12. Naturally, the present invention could also apply to a different pump or to a valve with a valve member that functions with a propellant gases. The dispenser member, that is referred to below under the term pump 10, is actuated by a dispenser head 30 that is mounted on said pump. In the embodiment shown in the figures, the dispenser head 30 is a nasal dispenser head including an axial extension that is provided with a spray orifice 31 and that is for inserting into a nostril.

Figure 2:
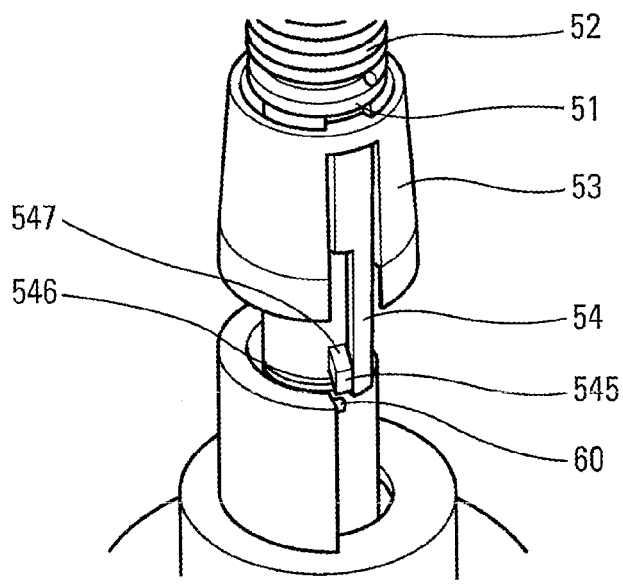
FIG. 2 is a diagrammatic and fragmentary perspective view of a portion of the FIG. 1 device.
Figure 3:
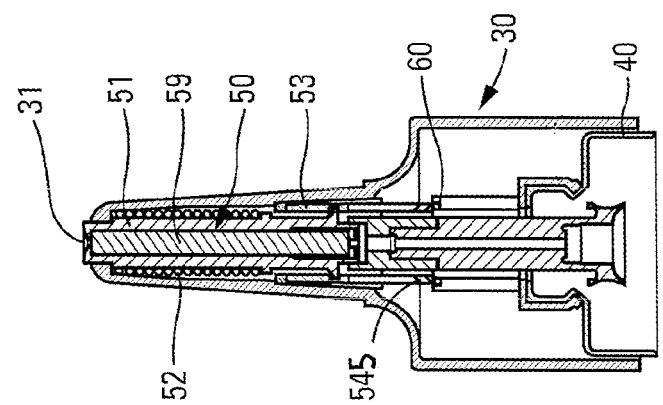
FIG. 3 is a view similar to the view in FIG. 1, in the indicating position, before actuation of the dispenser member.
Figure 4:
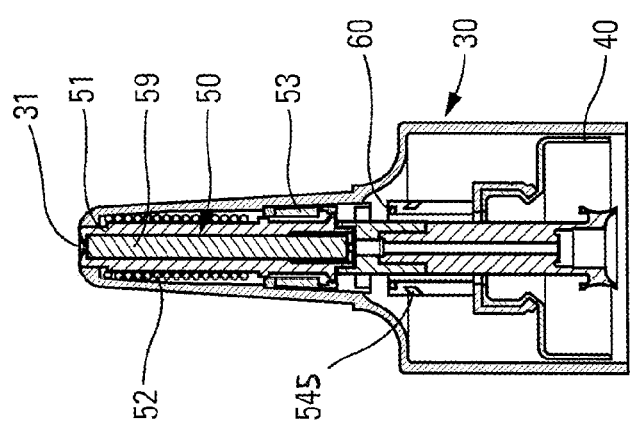
FIG. 4 is a view similar to the view in FIG. 3, at the very start of actuation of the dispenser member.
Figure 5:
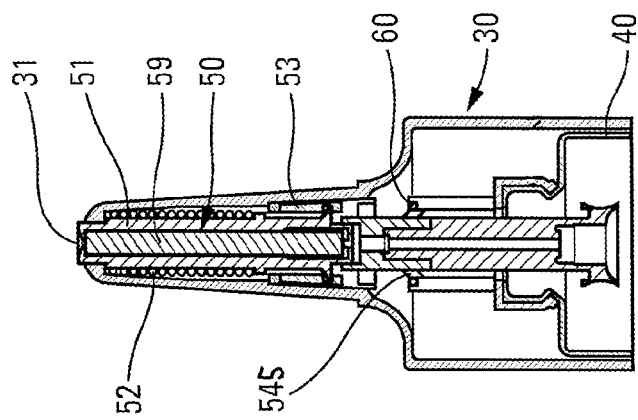
FIG. 5 is a view similar to FIGS. 3 and 4, after fluid has been dispensed.

In the invention, visual indicator means 50 are provided, preferably arranged inside the dispenser head 30. In the embodiment shown, the visual indicator means 50 include a movable member 51 that is movable between an indicating position and a non-indicating position. In the indicating position, that is shown diagrammatically in FIGS. 3 and 5, said movable member 51 projects axially out from the dispenser head 30. The portion that projects out from the head thus forms visual indicator means that can be seen by the user from the outside. For example, the side surface of said movable member 51 could be of a color that is different from the color of the head, so that the user could very easily see whether or not the movable member projects out from the head. Naturally, it is also possible to imagine a viewing window in the dispenser member 30, and visual marks on the movable member, e.g. portions of different colors that are visible through said window depending on the indicating or non-indicating position of said movable member 51. The movable member 51 is urged towards its non-indicating position by a spring 52. A blocking element 53 is provided so as to hold the movable member 51 in its indicating position in spite of the resilient force exerted by the spring 52. The blocking element 53 may be formed by a sleeve that is arranged radially outside said movable member 51, and that cannot move axially in the dispenser head 30. In other words, the movable member 51 moves axially inside said blocking element 53. In the indicating position, said blocking element 53 co-operates with the movable member 51 so as to hold it in that position. Advantageously, the blocking element 53 includes at least one flexible tab 54 that is provided with an inner profile 541 that is adapted to co-operate with an outer radial projection 511 of the movable member 51. As can be seen in FIGS. 3 and 5, the inner profile 541 holds the movable member 51 in its indicating position. In addition, the tab 54 is also adapted to co-operate with a cam 60. The cam 60 is adapted to deform the tab 54 radially outwards at the very start of actuating the pump 10. More precisely, as can be seen in FIG. 2, the cam 60 may be formed by a projection, preferably of rounded shape, against which the tab 54 comes to bear via an end projection 545 that is provided with a sloping bottom end surface 546, as can be seen in FIG. 3. From the start of the actuation stroke, the tab thus moves radially outwards by sliding along the cam 60. This radial deformation disengages the radial projection 511 of the movable member 51 from said inner profile 541 of the blocking element 53. Under the effect of the force of the spring 52, the movable member 51 is thus returned into its non-indicating position, shown in FIGS. 1 and 4, in which it does not project out from the dispenser head. When the movable member 51 is in its non-indicating position, its radial projection 511 keeps the tab 54 of the blocking element 53 deformed radially outwards. The actuation stroke of the pump thus continues, and the pump is actuated so as to dispense a dose of fluid. The fluid is thus expelled under pressure through the dispenser head, and when the fluid under pressure arrives at the movable member 51, the pressure is sufficient to return said movable member 51 into its indicating position, against the force exerted by the spring 52. Typically, the fluid pressure at the outlet from the pump is about 5 bars, or more. When the movable member 51 is returned into its indicating position, the tab 54 of the blocking element 53 resiliently returns into its blocking position. In the actuated position of the dispenser head, the end projection 545 is located axially on the other side of the cam 60. At the end of actuation, when the user relaxes the pressure on the dispenser head, the dispenser head rises, in particular under the effect of the return spring of the pump. During this rise, the flexible tab 54 once again co-operates with the cam 60 via a sloping top surface 547 of the end projection 545 that deforms the flexible tab 54 radially inwards, so as to continue to block the movable member 51 in its indicating position. The movable member thus remains in its indicating position until the next actuation. Advantageously, the blocking element 53 may comprise two diametrally-opposite flexible tabs 54.

In the particular embodiment shown, the movable member 51 is hollow and defines the expulsion channel and the spray orifice 31 of the dispenser head 30. Advantageously, an insert 59 is arranged in stationary manner inside said movable member 51, and thus moves jointly with said movable member between the indicating and non-indicating positions. In conventional manner, the insert 59 serves to define a spray profile (not shown) at the spray orifice 31, so as to ensure that the fluid dispensed is sprayed properly.

Typically, with a nasal dispenser pump, the fluid is dispensed after a stroke of about 3.5 millimeters (mm) from the rest position of the pump. The present invention causes the movable member 51 to return towards the non-indicating position at the very start of the actuation stroke, and advantageously before the end of the first millimeter of actuation stroke. It is thus guaranteed that the movable member 51 is returned to its non-indicating position before the dose of fluid starts to be dispensed. Thus, if there is a malfunction in the pump or if actuation is not performed correctly, and the dose is not dispensed, then the movable member 51 remains in its non-indicating position, so as to inform the user that the dose has not been expelled.

Although the present invention is described above with reference to a particular embodiment thereof, various modifications could naturally be applied thereto without going beyond the ambit of the present invention, as defined by the accompanying claims.

The invention claimed is:

1. A fluid dispenser device comprising:
   a dispenser member that is mounted on a fluid reservoir for containing a fluid and that is actuated by a dispenser head that includes a spray orifice,
   visual indicator means that are movable between an indicating position and a non-indicating position, said visual indicator means configured to be moved into the non-indicating position at the start of each actuation of said dispenser member, and moved from said non-indicating position towards said indicating position by said fluid, while said fluid is being dispensed,
   said visual indicator means including a movable member that is urged by a spring towards the non-indicating position, and that is configured to be urged by the pressure of the fluid during dispensing towards the indicating position,
   wherein said movable member is blocked in the indicating position by a blocking element that is urged resiliently towards a blocking position.

2. A fluid dispenser device according to claim 1, wherein said visual indicator means are arranged inside said dispenser head, and can be seen, at least in part, from the outside, in the indicating position.

3. A fluid dispenser device according to claim 1, wherein said blocking element is released from the blocking position at the start of actuation of the dispenser member, thereby enabling the movable member to return to the non-indicating position, under the effect of said spring.

4. A fluid dispenser device according to claim 3, wherein said blocking element includes at least one flexible tab that is provided with an inner profile that co-operates with a radial projection of said movable member so as to hold said movable member in the indicating position.

5. A fluid dispenser device according to claim 4, wherein said at least one flexible tab includes an end projection that, at the start of actuation of the dispenser member, co-operates with a cam that is adapted to deform said at least one flexible tab radially outwards, eliminating said co-operation between the inner profile of the at least one flexible tab and the radial projection of the movable member.

6. A fluid dispenser device according to claim 5, wherein said end projection includes a sloping bottom end surface that co-operates with the cam at the start of actuation so as to deform each flexible tab radially outwards, and a sloping top surface that co-operates with the cam after actuation so as to deform each flexible tab radially inwards while the dispenser head is returning to a rest position.

7. A fluid dispenser device according to claim 5, wherein said cam is formed by a rounded projection that is secured to the reservoir, in particular that is secured to a fastener ring that fastens the dispenser member on said reservoir.

8. A fluid dispenser device according to claim 1, wherein said movable member is hollow and defines said spray orifice of the fluid dispenser device.

9. A fluid dispenser device according to claim 8, wherein said movable member projects axially out from said dispenser head in the indicating position, a portion projecting out from the dispenser head forming a visual indicator that can be seen from the outside.

10. A fluid dispenser device according to claim 8, wherein said movable member contains an insert that cannot move relative to said movable member.

11. A fluid dispenser device according to claim 1, wherein said dispenser head is a nasal head including an axial extension for penetrating into a user's nostril.

* * * * *